US009081303B2

(12) United States Patent
Cramer et al.

(10) Patent No.: US 9,081,303 B2
(45) Date of Patent: Jul. 14, 2015

(54) METHODS AND SCATTEROMETERS, LITHOGRAPHIC SYSTEMS, AND LITHOGRAPHIC PROCESSING CELLS

(75) Inventors: Hugo Augustinus Joseph Cramer, Eindhoven (NL); Arie Jeffrey Den Boef, Waalre (NL); Henricus Johannes Lambertus Megens, Waalre (NL); Hendrik Jan Hidde Smilde, Veldhoven (NL); Adrianus Johannes Hendrikus Schellekens, Liempde (NL); Michael Kubis, Dresden (DE)

(73) Assignee: ASML Netherlands B.V., Veldhoven (NL)

( * ) Notice: Subject to any disclaimer, the term of this patent is extended or adjusted under 35 U.S.C. 154(b) by 850 days.

(21) Appl. No.: 12/846,652

(22) Filed: Jul. 29, 2010

(65) Prior Publication Data

US 2011/0027704 A1 Feb. 3, 2011

Related U.S. Application Data

(60) Provisional application No. 61/230,331, filed on Jul. 31, 2009.

(51) Int. Cl.
*G03F 7/20* (2006.01)
*G01B 11/24* (2006.01)
(Continued)

(52) U.S. Cl.
CPC ............ *G03F 7/70641* (2013.01); *G01B 11/24* (2013.01); *G01B 11/30* (2013.01);
(Continued)

(58) Field of Classification Search
None
See application file for complete search history.

(56) References Cited

U.S. PATENT DOCUMENTS 5,963,329 A 10/1999 Conrad et al.

6,451,700 B1 9/2002 Stirton et al.
(Continued)

FOREIGN PATENT DOCUMENTS

CN 101114135 A 1/2008
EP 1 628 164 A2 2/2006
(Continued)

OTHER PUBLICATIONS

International Search Report and Written Opinion directed to related International Patent Application No. PCT/EP2010/060894, mailed Nov. 18, 2010 form the International Searching Authority, European Patent Office, Rijswijk, Netherlands; 15 pages.
(Continued)

*Primary Examiner* — Gordon Stock, Jr.
(74) *Attorney, Agent, or Firm* — Sterne, Kessler, Goldstein & Fox P.L.L.C.

(57) ABSTRACT

In a method of determining the focus of a lithographic apparatus used in a lithographic process on a substrate, the lithographic process is used to form a structure on the substrate, the structure having at least one feature which has an asymmetry in the printed profile which varies as a function of the focus of the lithographic apparatus on the substrate. A first image of the periodic structure is formed and detected while illuminating the structure with a first beam of radiation. The first image is formed using a first part of non-zero order diffracted radiation. A second image of the periodic structure is formed and detected while illuminating the structure with a second beam of radiation. The second image is formed using a second part of the non-zero order diffracted radiation which is symmetrically opposite to the first part in a diffraction spectrum. The ratio of the intensities of the measured first and second portions of the spectra is determined and used to determine the asymmetry in the profile of the periodic structure and/or to provide an indication of the focus on the substrate. In the same instrument, an intensity variation across the detected portion is determined as a measure of process-induced variation across the structure. A region of the structure with unwanted process variation can be identified and excluded from a measurement of the structure.

24 Claims, 11 Drawing Sheets

(51) Int. Cl.
*G01B 11/30* (2006.01)
*G01N 21/47* (2006.01)
*G01B 11/02* (2006.01)
*G01B 11/22* (2006.01)
*G01N 21/88* (2006.01)

(52) U.S. Cl.
CPC ........... *G01N 21/47* (2013.01); *G03F 7/70625* (2013.01); *G01B 11/02* (2013.01); *G01B 11/22* (2013.01); *G01N 21/88* (2013.01); *G03F 7/7065* (2013.01); *G03F 7/70608* (2013.01); *G03F 7/70633* (2013.01)

(56) References Cited

U.S. PATENT DOCUMENTS

| | | | |
|---|---|---|---|
| 6,762,111 | B2 | 7/2004 | Fukuda |
| 6,773,939 | B1 | 8/2004 | Wright |
| 6,780,574 | B2 | 8/2004 | Kawashima |
| 6,859,746 | B1 | 2/2005 | Stirton |
| 6,870,668 | B2 | 3/2005 | Ozawa |
| 6,980,300 | B1 | 12/2005 | Lensing et al. |
| 7,084,990 | B2 | 8/2006 | Sasazawa et al. |
| 7,508,976 | B1 | 3/2009 | Yang et al. |
| 7,515,279 | B2 | 4/2009 | Raymond |
| 7,528,941 | B2 * | 5/2009 | Kandel et al. ............... 356/237.2 |
| 7,528,966 | B2 | 5/2009 | Matsumoto |
| 7,532,331 | B2 | 5/2009 | Kiers et al. |
| 7,879,516 | B2 | 2/2011 | Kawachi et al. |
| 7,961,296 | B2 | 6/2011 | Finders |
| 8,411,287 | B2 * | 4/2013 | Smilde et al. ............... 356/620 |
| 8,553,227 | B2 * | 10/2013 | Jordanoska ................. 356/369 |
| 8,553,230 | B2 * | 10/2013 | Den Boef et al. ............. 356/453 |
| 8,786,825 | B2 * | 7/2014 | Van De Kerkhof et al. .... 355/67 |
| 8,797,554 | B2 * | 8/2014 | Straaijer ....................... 356/625 |
| 8,830,447 | B2 * | 9/2014 | Den Boef et al. ............. 355/55 |
| 8,867,020 | B2 * | 10/2014 | Smilde et al. ................ 355/67 |
| 8,908,147 | B2 * | 12/2014 | Den Boef et al. ............. 355/53 |
| 2002/0048018 | A1 | 4/2002 | Fujimoto |
| 2003/0048458 | A1 | 3/2003 | Mieher et al. |
| 2004/0004726 | A1 | 1/2004 | Sezginer et al. |
| 2004/0190008 | A1 * | 9/2004 | Mieher et al. ................ 356/625 |
| 2005/0225695 | A1 | 10/2005 | Arai et al. |
| 2005/0275848 | A1 | 12/2005 | Hill |
| 2006/0033921 | A1 * | 2/2006 | Den Boef et al. ............. 356/446 |
| 2006/0066855 | A1 * | 3/2006 | Boef et al. .................... 356/401 |
| 2007/0003840 | A1 * | 1/2007 | Van Der Schaar et al. ........ 430/5 |
| 2007/0279630 | A1 | 12/2007 | Kandel et al. |
| 2008/0018897 | A1 | 1/2008 | Littau |
| 2008/0074665 | A1 | 3/2008 | Brill et al. |
| 2008/0239265 | A1 | 10/2008 | Den Boef |
| 2008/0279442 | A1 * | 11/2008 | Den Boef et al. ............. 382/144 |
| 2009/0116035 | A1 | 5/2009 | Shyu et al. |
| 2009/0296075 | A1 | 12/2009 | Hu et al. |
| 2010/0201963 | A1 | 8/2010 | Cramer et al. |
| 2011/0102753 | A1 * | 5/2011 | Van De Kerkhof et al. .... 355/27 |
| 2011/0131007 | A1 | 6/2011 | Huang et al. |
| 2011/0249247 | A1 | 10/2011 | Cramer et al. |
| 2011/0310388 | A1 * | 12/2011 | Hill et al. ....................... 356/369 |
| 2012/0044472 | A1 | 2/2012 | Den Boef et al. |
| 2012/0120396 | A1 * | 5/2012 | Kandel et al. ................ 356/399 |
| 2012/0206703 | A1 * | 8/2012 | Bhattacharyya et al. ........ 355/53 |
| 2012/0242970 | A1 * | 9/2012 | Smilde et al. .................... 355/77 |
| 2013/0050501 | A1 * | 2/2013 | Warnaar et al. ............... 348/169 |
| 2013/0100427 | A1 * | 4/2013 | Koolen et al. ................... 355/67 |
| 2013/0162996 | A1 | 6/2013 | Straaijer et al. ............... 356/369 |
| 2013/0258310 | A1 * | 10/2013 | Smilde et al. .................... 355/77 |
| 2013/0308142 | A1 * | 11/2013 | Straaijer ....................... 356/625 |
| 2014/0139814 | A1 | 5/2014 | Cramer et al. |

FOREIGN PATENT DOCUMENTS

| | | |
|---|---|---|
| JP | 2001-319874 A | 11/2001 |
| JP | 2002-131185 A | 5/2002 |
| JP | 2003-224057 A | 8/2003 |
| JP | 2003-344029 A | 12/2003 |
| JP | 2006-013449 A | 1/2006 |
| JP | 2008-102125 A | 5/2008 |
| JP | 2008-171960 A | 7/2008 |
| JP | 2008-294094 A | 12/2008 |
| JP | 2009-295976 A | 12/2009 |
| JP | 2010-079166 A | 4/2010 |
| WO | WO 02/31570 A1 | 4/2002 |
| WO | WO 03/001297 A2 | 1/2003 |
| WO | WO 2009/078708 A1 | 6/2009 |
| WO | WO 2009/129974 A1 | 10/2009 |
| WO | WO 2010/076232 A2 | 7/2010 |
| WO | WO 2010/130600 A1 | 11/2010 |
| WO | WO 2013178422 A1 * | 12/2013 |
| WO | WO 2013189724 A1 * | 12/2013 |
| WO | WO 2014026819 A2 * | 2/2014 |

OTHER PUBLICATIONS

English-Language Abstract for Japanese Patent Publication No. 2010-079166 A, published Apr. 8, 2010; 1 page.

English-Language Abstract for Japanese Patent Publication No. 2006-013449 A, published Jan. 12, 2006; 1 page.

English-Language Abstract for Chinese Patent Publication No. 101114135 A, published Jan. 30, 2008; 1 page.

U.S. Appl. No. 14/149,723, Cramer et al., "Methods and Scatterometers, Lithographic Systems, and Lithographic Processing Cells," filed Jan. 7, 2014.

Non-Final Rejection mailed Mar. 13, 2014 for U.S. Appl. No. 14/149,723, filed Jan. 7, 2014; 14 pages.

Non-Final Rejection mailed Jun. 18, 2014 for U.S. Appl. No. 14/149,723, filed Jan. 7, 2014; 16 pages.

Notice of Allowance mailed Dec. 30, 2014 for U.S. Appl. No. 14/149,723, filed Jan. 7, 2014; 11 pages.

* cited by examiner

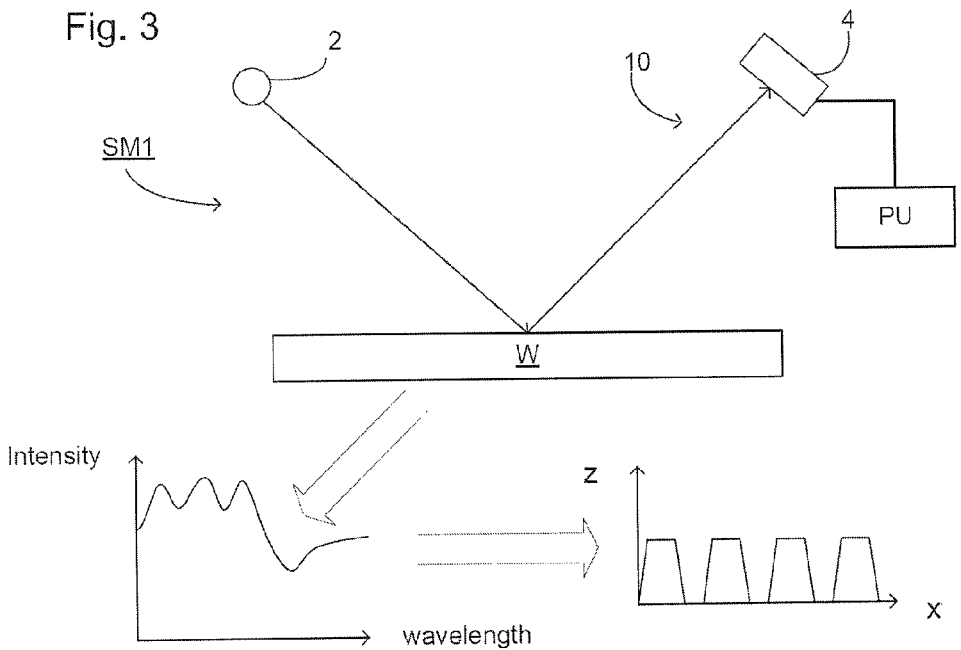
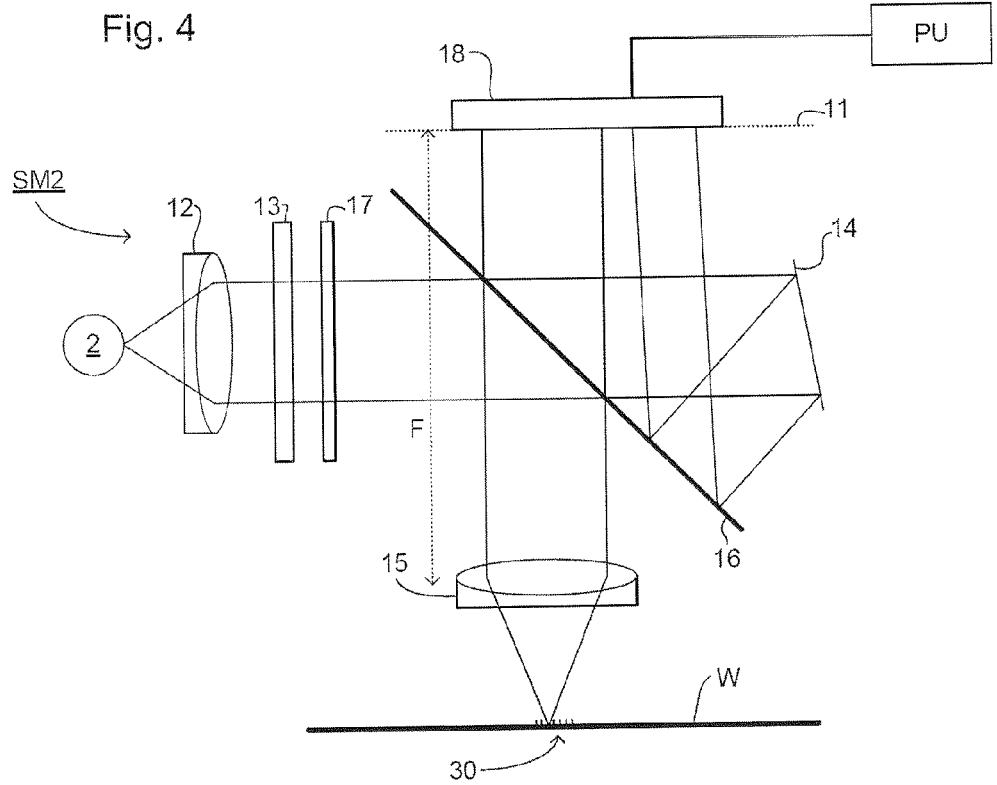

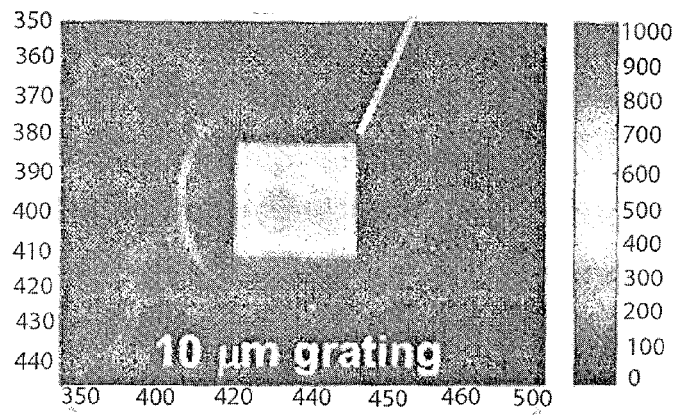
Fig. 9(b)
Fig. 9(a)
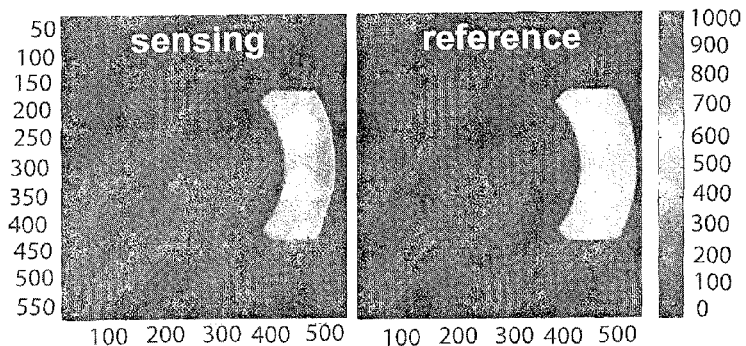
Fig. 10(a)    Fig. 10(b)

METHODS AND SCATTEROMETERS, LITHOGRAPHIC SYSTEMS, AND LITHOGRAPHIC PROCESSING CELLS

CROSS REFERENCE TO RELATED APPLICATIONS

This application claims priority under 35 U.S.C. §119(e) to U.S. Provisional Patent Application No. 61/230,331, filed Jul. 31, 2009, which is incorporated by reference herein in its entirety.

BACKGROUND

1. Field of the Invention

The present invention relates to methods and scatterometers usable, for example, in the manufacture of devices by lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Scatterometers may be used to measure several different embodiments of lithographic apparatuses, including their positioning errors of the substrate prior to exposure and exposure efficacy. Two important parameters of a lithographic apparatus (and specifically of the exposure action that the lithographic apparatus carries out) that may also be measured by scatterometers are focus and dose. A lithographic apparatus has an exposure apparatus that includes a radiation source and a projection system as mentioned below. The radiation source provides a beam of radiation and the projection system focuses the beam of radiation and applies a pattern to the beam to create a patterned beam of radiation that strikes the resist on the substrate surface. The dose of radiation that is projected onto a substrate in order to expose it, is controlled by various parts of the exposure apparatus. It is mostly the projection system of the lithographic apparatus that is responsible for the focus of the radiation onto the correct portions of the substrate. It is important that the focusing of the image of the pattern in the patterned radiation occurs at the surface of the substrate where the exposure occurs. This is so that the sharpest (i.e., most focused) image will occur on the surface of the substrate and the sharpest pattern possible may be exposed thereon. This enables smaller product patterns to be printed.

The focus and dose of the radiation directly affect various parameters of the patterns or structures that are exposed on the substrate. Parameters that can be measured using a scatterometer are physical properties of structures within the patterns that have been printed onto a substrate. These parameters may include the critical dimension (CD) or sidewall angle (SWA). The critical dimension is effectively the mean width of a structure such as a bar (or a space, dot or hole, depending on what the measured structures are that are in the printed pattern). The sidewall angle is the angle between the surface of the substrate and part of the rising (or falling) portion of the structure.

In addition, mask shape corrections (focus corrections for correcting for the bending of a mask) can be applied if scribe lane structures are used with a product mask for focus measurements.

It is desirable to provide a method of measuring focus using a scatterometer wherein the size of the target may be made smaller than the radiation beam spot.

Smaller markers for positioning, overlay- and CD-metrology, and focus dose metrology reduce real estate consumption for metrology. Smaller targets are more sensitive for etch process micro-loading and other process effects like non-conformal deposition and chemical and mechanical polishing. The complex processes of lithography and especially etch processes such as reactive-ion-etching (RIE) or plasma etching result for example in a (product) environment dependency of the etch rate (etch proximity). These micro-loading and process effects at (sub-)micrometer scale are undesirable for the production of semiconductor devices, and may perturb metrology on small targets differently than product features or differently over the width of the target. Particularly non-uniformity at the target-edge can cause metrology problems for overfill illumination, where the detection beam is larger than the target, combined with pupil-detection in optical metrology.

Micro-loading and process effects on metrology targets are difficult to detect because it concerns properties that occur within the processed layers of a wafer, for example the local etch rate for the bottom-grating of an overlay diffraction grating.

Detection of such micro-loading and process effects on metrology targets requires the application of an additional measurement technique such as scanning electron microscopy (SEM) or optical microscopy. However, these techniques have a limited sensitivity with respect to profile asymmetries of measured structures. Specific disadvantages of optical microscopy and top-down SEM are:

i. they are an additional "inspection" measurement;

ii. they need in most cases a different measurement tool than the actual metrology measurement using the inspected metrology targets;

iii. they give only limited information about profile asymmetries and their variations within the metrology target; and iv. they cannot be used to improve the measurement of the actual target, they can only help for deciding if a metrology target can be used or not for a measurement.

Other methods to detect and study micro-loading and process-effects are transmission electron microscopy (TEM) and cross-section SEM. These have access to the profile information of the structured layers. However, both are time-consuming, destructive techniques because the wafer has to be cut along a line at the structure of interest for the cross-sectional view. Furthermore, only a single local cross-section can be prepared; TEM and cross-section SEM do not allow for extraction of 2-dimensional information locally over the wafer field.

Scanning Probe Microscopy (SPM) techniques such as Atomic Force Microscopy (AFM) on the freshly etched structure without top-layers is another possible inspection technique. However the technique is rather slow and it interrupts the production of wafers. The measurement is furthermore performed at an unfinished target, while one would like to know the effects in the complete layer structure.

Also, diffraction-based reconstruction via pupil detection may be a candidate technique to observe process effects. However, diffraction-based pupil detection combined with reconstruction is only able to probe process-effects on a large scale of the order of the illumination spot size (tens of microns). For pupil detection, the local information at submicron scale is hardly accessible (unless entire targets or structures are completely reconstructed, using for example an electro-magnetic solver in a recurrent solving loop, however that requires an unfeasible number of fit parameters describing e.g., the side-wall-angle of each individual line in the grating structure). Furthermore, the reconstruction necessary to retrieve the inspection information is time-expensive.

It is desirable to provide a method of detecting such micro-loading and process effects on metrology targets.

SUMMARY

According to an aspect of the present invention there is provided a method of determining the focus of a lithographic apparatus used in a lithographic process on a substrate, comprising the following steps. Using the lithographic process to form a structure on the substrate, the structure having at least one feature which has a profile which has an asymmetry which depends on the focus of the lithographic apparatus on the substrate. A first measurement step comprising forming and detecting a first image of the periodic structure while illuminating the structure with a first beam of radiation, the first image being formed using a first part of non-zero order diffracted radiation while excluding zero order diffracted radiation. A second measurement step comprising forming and detecting a second image of the periodic structure while illuminating the structure with a second beam of radiation, the second image being formed using a second part of the non-zero order diffracted radiation which is symmetrically opposed to the first part in a diffraction spectrum. Using the first and second images detected in the first and second measurements to determine the asymmetry in the profile of the periodic structure and/or to provide an indication of the focus on the substrate.

In one example, 'symmetrically opposed' parts of the diffraction spectrum will be understood as referring to rays diffracted at the same angle relative to a specular reflected ray (zero order diffracted ray), but in opposite directions. The first and second symmetrically opposed parts of non-zero order diffracted radiation may for example comprise substantially the +1 and −1 order diffracted radiation respectively (or vice versa). In a practical system, a range of angles will be admitted, rather than a single angle. Provided the ranges of angles are symmetrical about the zero order, any inequality in their intensities is assumed to be a consequence of asymmetry in the diffracting structure. Note that the zero order diffracted ray may not be normal to the substrate surface, but may be incident at an angle. The diffraction orders which contribute to the images can be varied by varying the angle of illumination, instead of or in addition to varying the angle at which rays are detected.

In one embodiment, in an optical system used in the measurements, the first and second beams of radiation have angles of incidence on the periodic structure which are symmetrically off-axis with respect to the optical system, and the first and second images are formed and detected using that radiation which is diffracted by the periodic structure into a narrower range of angles centered on the optical axis.

According to another aspect of the present invention, there is provided angularly resolved scatterometer configured to determine the focus of a lithographic apparatus used in a lithographic process on a substrate, wherein the lithographic process is used to form a structure on the substrate, the structure having at least one feature which has a profile which has an asymmetry which depends on the focus of the lithographic apparatus on the substrate, the scatterometer comprising: an illumination arrangement operable to deliver first and second beams of radiation to the substrate for use in first and second measurements, a detection arrangement operable during the first and second measurements to form and detect respective first and second images of the substrate using radiation diffracted from the substrate, and a stop arrangement within the detection arrangement. The illumination arrangement and stop arrangement together are effective to stop zero order diffracted radiation contributing to the first and second images, while the first and second images are formed using first and second parts respectively of the non-zero order diffracted radiation, the first and second parts being symmetrically opposite one another in a diffraction spectrum of the diffracted radiation. The scatterometer further comprises a computational arrangement operable to determine the profile asymmetry for the feature from the first and second images and/or to use the determined asymmetry and the relationship between the focus and the asymmetry for each feature to provide an indication of the focus on the substrate.

Another embodiment of the present invention further provides a lithographic system comprising: a lithographic apparatus comprising: an illumination optical system arranged to illuminate a pattern, a projection optical system arranged to project an image of the pattern on to a substrate, and The angularly resolved scatterometer according to the present invention as set forth above.

A further embodiment of the present invention further provides a lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and The scatterometer according to the present invention as set forth above.

According to yet another aspect of the present invention there is provided a method of detecting process-induced variation in a structure on a substrate, the method comprising: directing a beam of radiation onto the substrate so as to illuminate the structure and to form an image, selectively detecting a portion of the image while preventing all except one order of diffracted radiation from being detected, determining an intensity variation across the detected portion, corresponding to variation in diffraction efficiency across the structure, and identifying process-induced variation in the structure using the determined intensity variation.

According to a still further aspect of the present invention there is provided The angularly resolved scatterometer configured to determine process-induced variation in a structure on a substrate, the angularly resolved scatterometer comprising: an illumination device operable to produce a beam of radiation, a directing device configured to direct the beam of radiation onto the substrate to illuminate the structure, a detection device configured to detect radiation diffracted from the substrate and to form an image, a stop device between the substrate and the detection device, the stop device being configured to stop all except one order of diffracted radiation from being detected by the detection device, and a computational arrangement operative to determine an intensity variation across the detected radiation, corresponding to variation in diffraction efficiency across the structure, and to identify process-induced variation in the structure using the determined intensity variation.

According to an even further aspect of the present invention there is provided a lithographic system comprising: a lithographic apparatus comprising: an illumination optical system arranged to illuminate a pattern, a projection optical system arranged to project an image of the pattern on to a substrate, and an angularly resolved spectrometer comprising: an illumination device operable to produce a beam of radiation, a directing device configured to direct the beam of radiation onto the substrate to illuminate the structure, a detection device configured to detect radiation diffracted from the substrate and to form an image, a stop device between the substrate and the detection device, the stop device being configured to stop all except one order of diffracted radiation from being detected by the detection device, and a computational arrangement operative to determine an intensity variation across the detected radiation, corresponding to variation in diffraction efficiency across the structure, and to identify process-induced variation in the structure using the determined intensity variation.

According to another yet further aspect of the present invention there is provided an lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and an angularly resolved spectrometer comprising: an illumination device operable to produce a beam of radiation, a directing device configured to direct the beam of radiation onto the substrate to illuminate the structure, a detection device configured to detect radiation diffracted from the substrate and to form an image, a stop device between the substrate and the detection device, the stop device being configured to stop all except one order of diffracted radiation from being detected by the detection device, and a computational arrangement operative to determine an intensity variation across the detected radiation, corresponding to variation in diffraction efficiency across the structure, and to identify process-induced variation in the structure using the determined intensity variation.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention:

FIG. 3 depicts a first scatterometer.

FIG. 4 depicts a second scatterometer.

FIG. 9(a) illustrates a measured image of the target.

FIG. 9(b) illustrates an enlarged portion of the image shown in FIG. 9(a) measured by the image detector of the scatterometer shown in FIG. 5.

FIG. 10(a) illustrates a measured spectrum measured by the scatterometer spectra detector of the scatterometer shown in FIG. 5.

FIG. 10(b) illustrates a reference spectrum for comparison with the measured spectra.

FIGS. 13(a) to 13(d) illustrate examples of process effects: (a) ideal regular grating, (b) etch loading, (c) CMP dishing, and (d) litho non-optimal array edge compensation.

Figure 14:
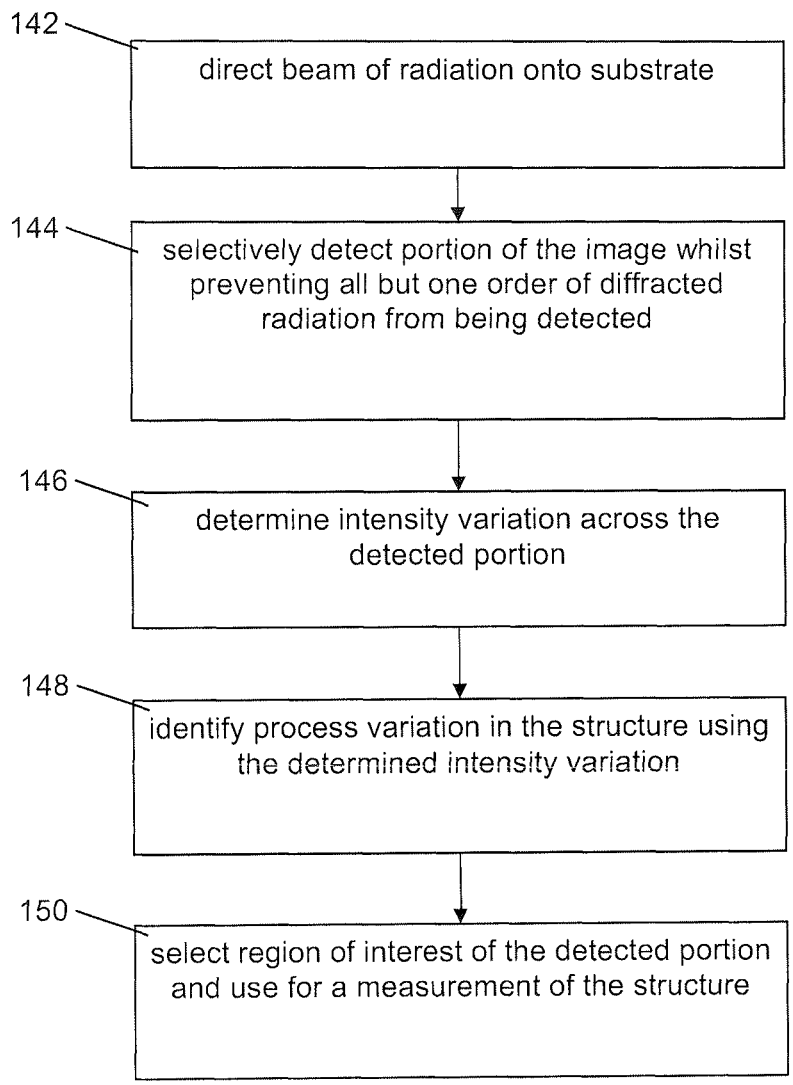

FIG. 14 is a flow chart showing a method in accordance with an embodiment of the present invention.

Figure 15:
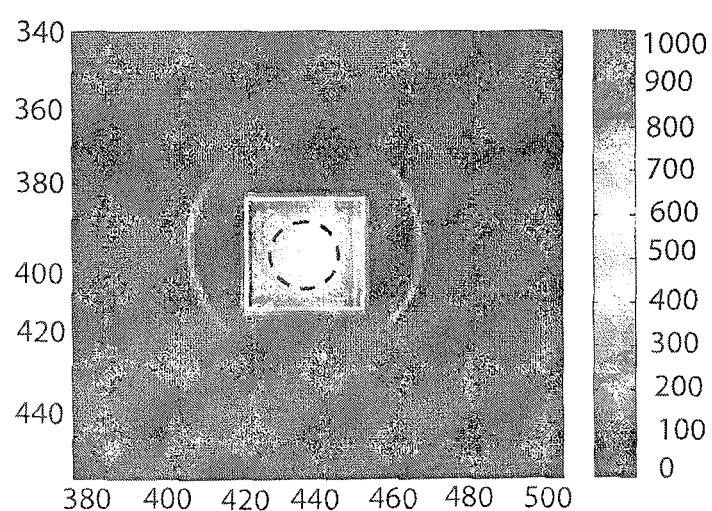

FIG. 15 illustrates selection of the region of interest (ROI) for metrology purposes.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a foam readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
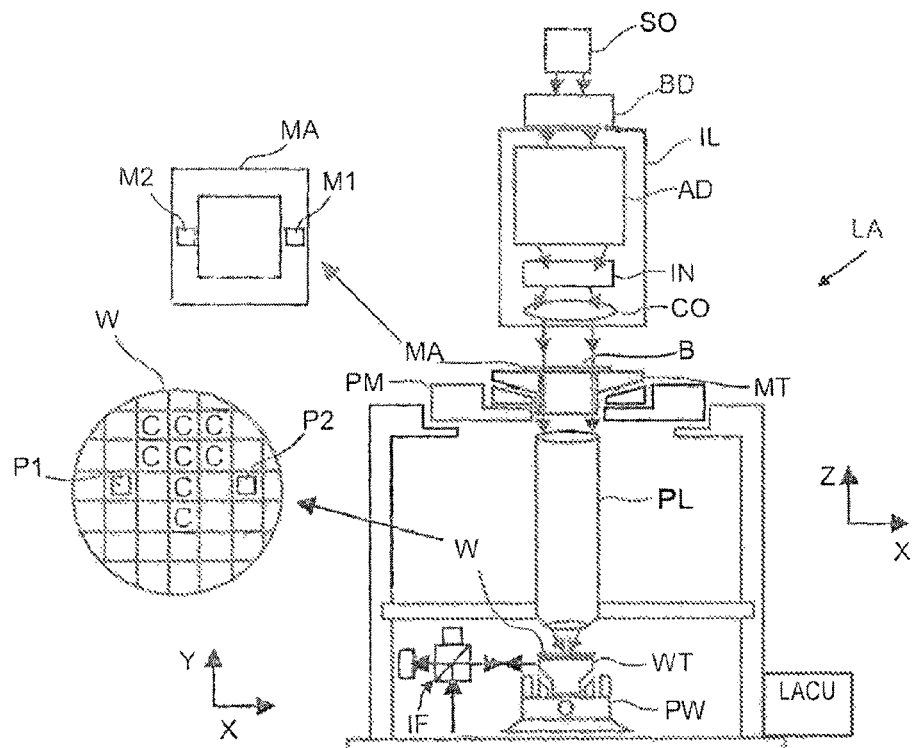
FIG. 1 depicts a lithographic apparatus.

FIG. 1 schematically depicts a lithographic apparatus. The apparatus comprises an illumination system (illuminator) IL configured to condition a radiation beam B (e.g., UV radiation or DUV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable minor arrays, and programmable LCD panels. Masks are well known in lithography, and include mask types such as binary, alternating phase-shift, and attenuated phase-shift, as well as various hybrid mask types. An example of a programmable minor array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
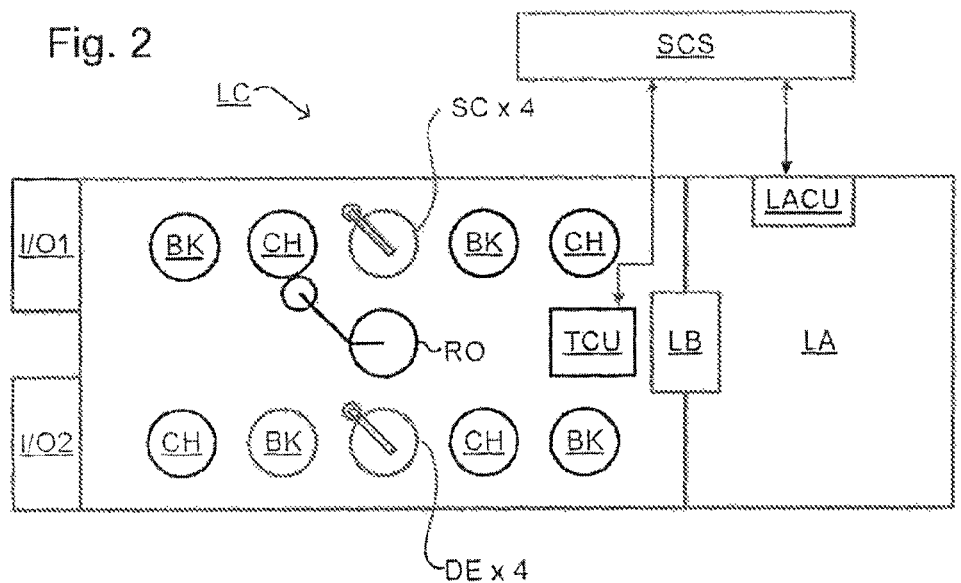
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist, which have been exposed to radiation, and those that have not—and not all inspection apparatus have sufficient sensitivity to make useful measurements of the latent image. Therefore measurements may be taken after the post-exposure bake step (PEB), which is customarily the first step, carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer SM1 that may be used in the present invention. It comprises a broadband (white light) radiation projector 2, which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used with the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence of the radiation in the object plane and the angular position defines the azimuth angle. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e., twice the bandwidth). Several "sources" of radiation can be different portions of an extended radiation source, which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP 1628164A, which is incorporated by reference here in its entirety.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

In a co-pending, co-assigned U.S. Provisional Patent Application 61/141,410, filed 30 Dec. 2008, the contents of which is incorporated herein by reference in its entirety, there is disclosed a method of measuring focus using the asymmetry in the higher orders of the scattered light, caused by an asymmetry in the profile of the printed target such as the different left and right side wall angles (SWAs) of a line structure in the target.

In a co-pending, co-assigned U.S. Provisional Patent Application 61/177,468, filed 12 May 2009, the contents of which is incorporated herein by reference in its entirety, there is disclosed a method of determining the relationship between the measured asymmetry in the scatterometry spectra and the focus. In the method two periodic structures are formed on a substrate by a lithographic apparatus, each structure having at least one feature, which has an asymmetry between opposing sidewall angles, which varies as a different function of the focus of the lithographic apparatus on the substrate. The ratio of the asymmetries for each of the features can be used to determine values for the focus on the substrate, which are independent of the processing conditions for the lithographic apparatus.

in either of the above-mentioned methods the size of the scatterometer target comprising the periodic structure may be larger than the radiation beam spot size on the substrate. This may impose a lower limit for the size of the target.

In accordance with an embodiment of the present invention there is provided a method of determining the focus of a lithographic apparatus using scatterometry spectra produced from a periodic structure produced on a wafer by the lithographic apparatus. In an embodiment of the present invention, the grating is illuminated by a beam having two different beam profiles in respective separate measurements, which in combination with a dark field measurement technique in which the zero order diffraction order from the periodic structure is blocked, enables the +1 and −1 order diffraction pattern to be measured in the two separate measurements.

Figure 5:
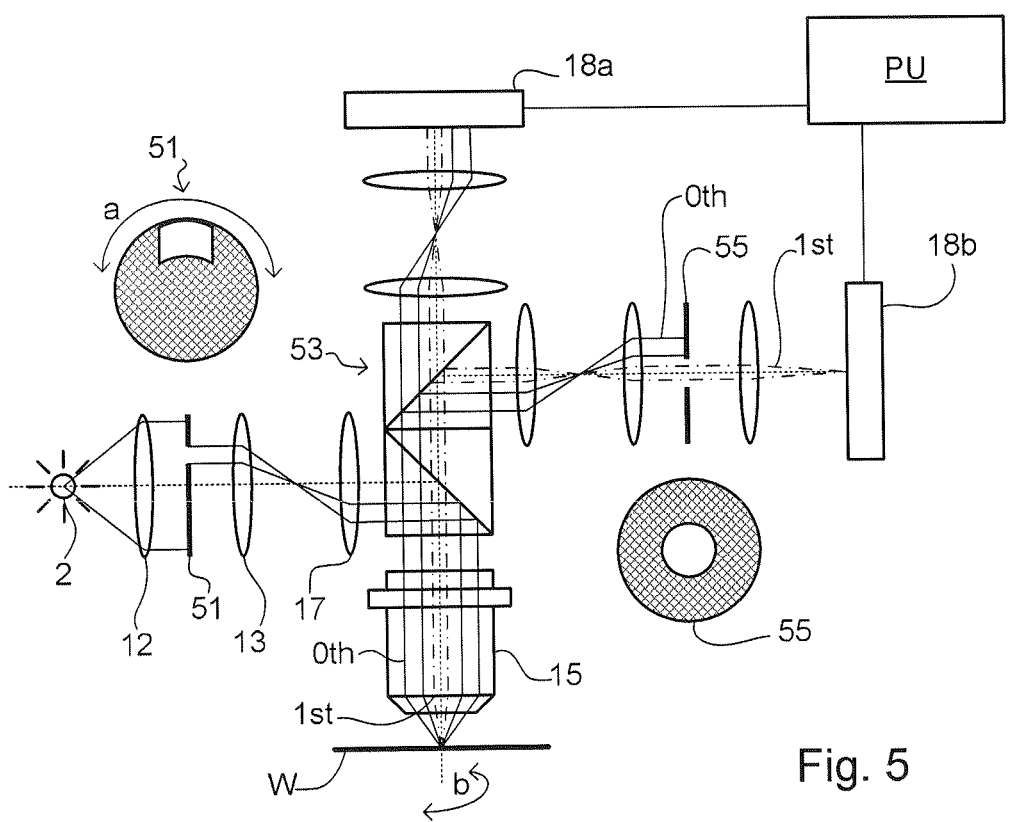
FIG. 5 depicts a scatterometer in accordance with an embodiment of the present invention.

Turning now to FIG. 5, this figure illustrates The angularly resolved scatterometer, which may be used in a method in accordance with an embodiment of the present invention. The scatterometer is designed along the same lines as that illustrated in FIGS. 3 and 4, and thus corresponding features are correspondingly labeled. However the scatterometer as illustrated in FIG. 5 differs from the scatterometer disclosed in FIGS. 3 and 4 in that a beam shaping arrangement 51 is provided between the radiation source 2 and the wafer W. Furthermore, the detector 18 is divided into a separate scatterometer spectrum detector 18a and an image detector 18b, a prism arrangement 53 being provided in the beam path from the wafer W so as to direct part of the diffracted beam from the wafer W onto the scatterometer sensor 18a and part of the beam diffracted from the wafer onto the image detector 18b. A spatial filter or field stop 55 is provided between the wafer W and the image detector 18b. In FIG. 5 the beam shaping arrangement 51 and the spatial filter or field stop 55 are also each shown in plan view.

The beam shaping arrangement 51 is designed so as to illuminate the target 30 on the wafer W at non-normal incidence. As can be best seen in the plan view of the beam shaping arrangement 51 in FIG. 5, this is made possible by an aperture, which is shown as a clear region in an otherwise opaque plate. As described in more detail in our co-pending U.S. Provisional Patent Application 61/151,665, which was filed on 11 Feb. 2009, the contents of which are hereby incorporated by reference in their entirety, a dark field detection method may be used in which the zero order diffraction order is blocked by the field stop 55. Thus, the only diffracted radiation which will reach the image detector 18b will be that of a selected higher diffraction order. In particular, either the −1 diffraction order as indicated in FIG. 6 or the +1 diffraction order as indicated in FIG. 7 may be selected by a 180° rotation of either the beam shaping arrangement 51 along the optical axis, that is along the direction a indicated in the cross sectional arrangement illustrated in FIG. 5, or alternatively by the rotation of the wafer W about the optical axis, as indicated by the rotation b in FIG. 5.

Figure 6:
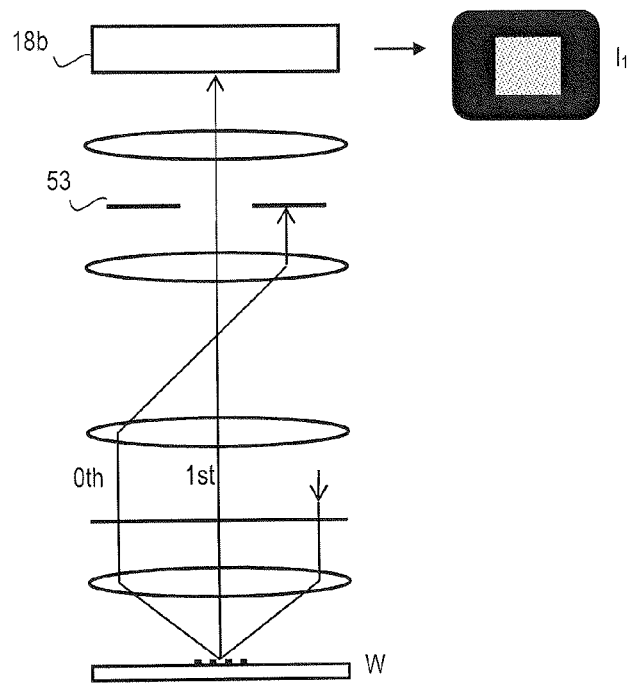
FIG. 6 depicts part of the operation of part of the scatterometer of FIG. 5.
Figure 7:
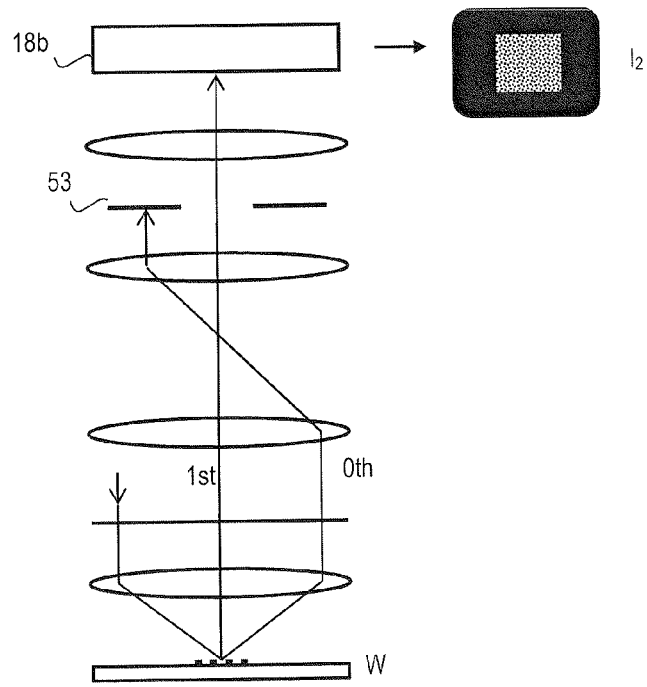
FIG. 7 depicts a different part of the operation of the scatterometer of FIG. 5.

Referring now to FIGS. 6 and 7, these figures indicate simplified versions of the optical path in the scatterometer illustrated in FIG. 5 in which either the −1st order diffracted radiation reaches the image detector 18b as illustrated in FIG. 6, or the +1st order diffracted reaches the image detector 18b as illustrated in FIG. 7. In either case the image, which is detected by the detector 18b, will show no modulation of the individual grating lines. Instead a homogenous intensity level $I_1$ in the case of FIG. 6 for the −1 diffraction order and $I_2$ in the case of FIG. 7 for the +1 diffraction order will be measured, the ratio of the intensity levels $I_1/I_2$ in each case being proportional to the ratio of the SWA asymmetry for the particular target 30. By measurement of the intensities $I_1$ and $I_2$ for the +1 and −1 order diffractions, it is possible to determine the asymmetry in the printed pattern and thus, by using a predetermined relationship between the asymmetry and the focus, to determine the focus for the lithographic apparatus which has been used to form the target 30 on the wafer W.

Figure 8:
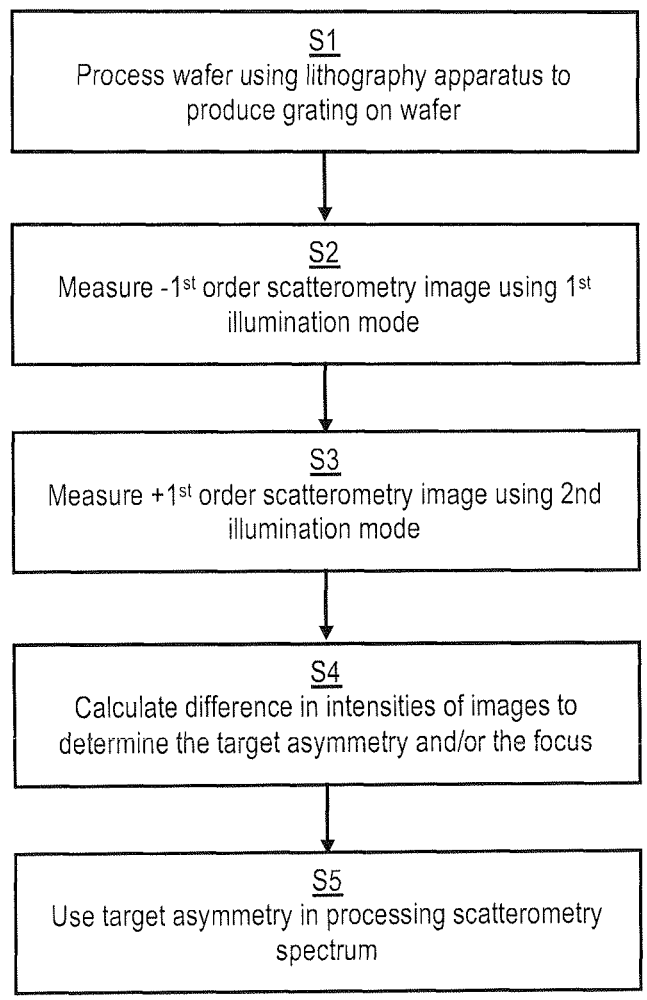
FIG. 8 is a flow chart showing a method in accordance with an embodiment of the present invention.

Turning now to FIG. 8, this figure illustrates a process in accordance with an embodiment of the present invention.

In step S1, the wafer is processed using the lithography apparatus to produce the target 30 in the form of the grating on the wafer W.

In step S2, using the scatterometer configuration shown in FIGS. 5 and 6 the $-1^{st}$ order scatterometry spectrum is measured by the image sensor 18b using the first illumination mode, that is with the beam shaping arrangement 51 and the wafer W in their first comparative positions.

In step S3 either the beam shaping arrangement 51, or the wafer W is rotated, to enable the $+1^{st}$ order scatterometry spectrum to be measured by the image sensor 18b.

In step S4 the ratio in intensities of the spectra $I_1$ and $I_2$ is calculated by processing unit PU to determine the focus of the wafer using a predetermined relationship between the focus and the difference in intensities. Alternatively the normalized difference between $I_1$ and $I_2$ can be used to determine the focus of the wafer.

For example, the relation between $I_1$, $I_2$ and wafer focus f may have the foil $$f - f_0 = C \frac{I_1 - I_2}{I_1 + I_2}$$

where C is a constant, f is the wafer focus, and $f_0$ is the wafer focus level that corresponds to zero asymmetry. C and $f_0$ can be determined by a calibration, using experimental or simulated data.

It is also possible to determine first the target asymmetry from $I_1$ and $I_2$. The focus can be calculated from the target asymmetry. Alternatively, the asymmetry is used directly to monitor and control the focus of the lithographic apparatus.

In the optional step S5 the target asymmetry is used in processing the scatterometry spectrum.

FIG. 9(a) shows the spectra detected at the image sensor 18b of FIGS. 6 and 7 in steps S2 or S3 in more detail. As can be seen from the enlarged detail in FIG. 9(b), the size of the spectra will be typically 30×30 pixels corresponding to a 10×10 μm grating. Thus this spectrum is comparatively easy to monitor to derive values of $I_1$ and $I_2$. Furthermore the size of the target 30 is not determined by the radiation beam spot size on the wafer W.

In the processing step of S5, the measured scatterometry spectrum illustrated in FIG. 10(a) will be processed to derive values of the substrate parameters, such as layer thicknesses, grating height and so on, typically by comparing the measured spectrum to a series of reference spectra as shown in FIG. 10(b), which may be either modeled spectra or spectra stored in a library as discussed above. In this process, the value of the target asymmetry derived in step S4 may be input as a known parameter.

It will be appreciated that the dark field measurement technique described above may also be used to determine the relationship between the difference in intensities $I_1$ and $I_2$ and the focus in an earlier calibration step, in which a number of gratings produced using different focus settings are produced on a calibration wafer and the diffraction spectra subsequently measured using a method in accordance with the present invention. Lithographic simulations may be used in the determination of the relationship between the difference in intensities and the focus. Alternatively the relationship between the asymmetry and the focus may be derived. Again lithographic simulations may be used in this determination.

It will be appreciated that due to diffraction, product features surrounding the grating may leak into the grating image. Thus the numerical aperture NA of the field stop 55 must be carefully chosen. The NA must be as large as possible to allow a sharp transition between the product area and the grating. However at the same time the stop 55 must block the zero order diffraction. Preferably the zero order diffracted image of the aperture defined by the beam shaping arrangement 51 and the open area of the field stop 55 are mutually exclusive, while the $1^{st}$ order diffracted image of the aperture, shifted in the pupil plane over a distance proportional to the ratio of the grating pitch and the radiation wavelength, is at least partially overlapping with the open area of the field stop 55. It is found that a value of NA of less than 0.4 is suitable, although this will depend on the grating parameters and the wavelength.

It will also be appreciated that measurement of the portions of the +1 and −1 order diffracted spectra is advantageous in a method in accordance with the present invention, as these give the most intense non-zero order diffracted spectra and are most sensitive to focus. However, in principle, the other higher order diffraction patterns can be used in a method in accordance with the present invention.

Furthermore, while the change of illumination direction in the embodiment described is achieved by rotation of the masking arrangement 51 by 180 degrees, it is possible alternatively to achieve the change in illumination direction rotate the substrate while maintaining the target structure within the field of view of objective lens 15, or to rotate the entire optical system. Furthermore, instead of providing a single mask 51 which rotates, a complementary pair of masks 51 could be provided and swapped, to achieve the same effect. A programmable illumination device such as a deformable mirror array can be used also. In these cases, some calibration may be required, to ensure that any asymmetry between the illumination modes is not mistaken for asymmetry in the structure 30.

It will also be appreciated that while in the particular embodiment described above, the masking arrangement 51 is designed such that only radiation which is off-axis is transmitted, in an alternative embodiment the masking arrangement 51 may be arranged so as to allow only radiation on and around the optical axis to be transmitted, with the spatial filter or field stop 55 being arranged such that only diffracted $-1^{st}$ order radiation in one measurement step, or $+1^{st}$ order radiation in the other measurement step, is detected by the image detector 18b. As just explained in relation to mask 51, the desired change of diffraction order can be achieved by rotating the field stop 55, or by substituting a second field stop having a complementary pattern, or by replacing the fixed field stop with a programmable spatial light modulator. While the optical system used for imaging in the present examples has a wide entrance pupil which is restricted by the field stop, in other embodiments the entrance pupil size of the imaging system itself may be small enough to restrict to the desired order, and thus serve also as the field stop.

An embodiment of the present invention is based on diffraction-based dark-field imaging on small targets and uses the ability to image the local diffraction efficiency of the structure, for a specified diffraction order, wavelength and angle of incidence.

In this embodiment, an image of the marker, (product) structure, or region of interest on the wafer is projected in the image-plane and recorded. The image is formed by one diffraction order only, while the other diffraction orders are blocked in an equivalent back-focal plane. No real image is projected; however the intensity values, such as grey scales, in the image indicate the local diffraction efficiency. The local diffraction efficiency is directly related to the local structure of marker, such as the etch-depth of trenches. An example of such a dark-field image of a 10 μm size targets is presented in FIG. 11, and cross-sections of such images in FIG. 12.

Figure 11:
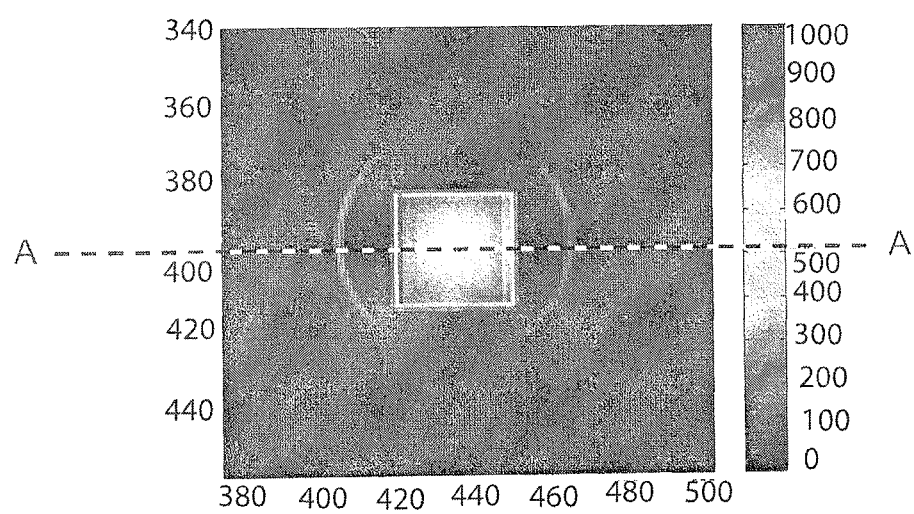
FIG. 11 illustrates a dark-field image based on one $1^{st}$ order diffraction of a 10-μm target consisting of vertical lines (stacked x-grating).

FIG. 11 illustrates a dark-field image based on one $1^{st}$ order diffraction of a 10-μm target consisting of vertical lines (stacked x-grating). The horizontal axis is the x-pixel coordinate and the vertical axis is the y-pixel coordinate. The grey scale is detected intensity. The cross section line AA is shown.

Figure 12:
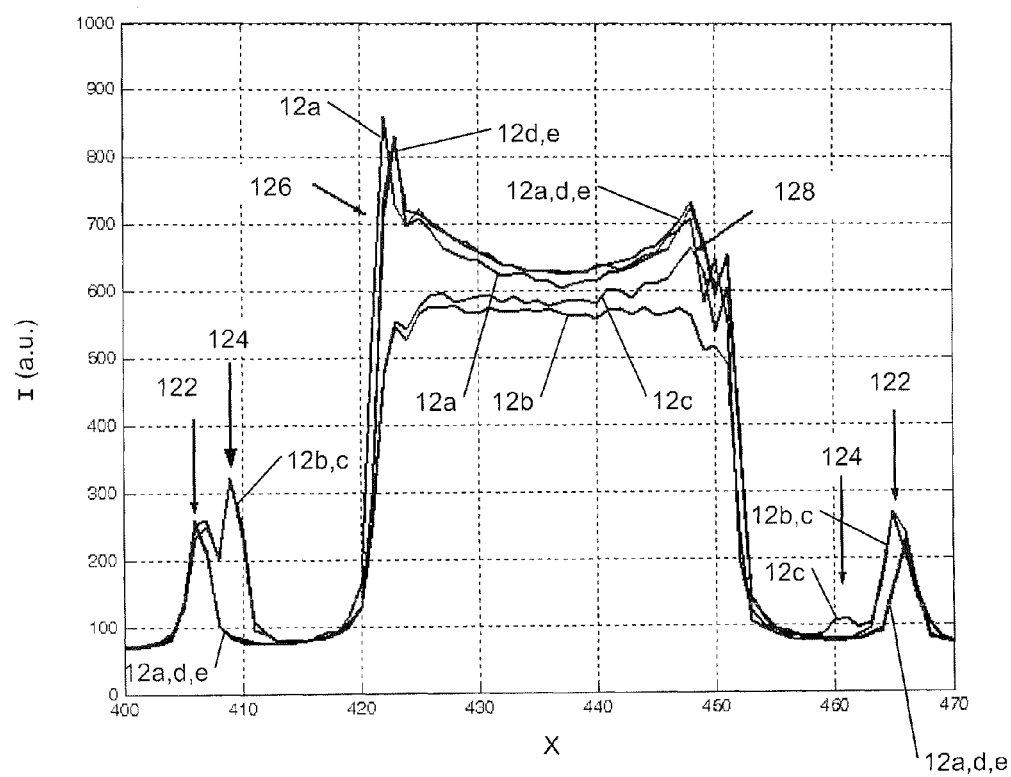
FIG. 12 illustrates horizontal cross sections of the dark-field images for 10 μm targets with environments that are unpatterned, lines, lines but with an unpatterned rectangle next to the grating (also referred to as "torture"), asymmetric contact holes and contact holes with an unpatterned rectangle next to the grating.
Figure 13A:
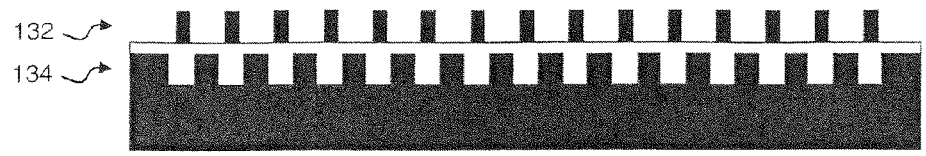
Figure 13B:
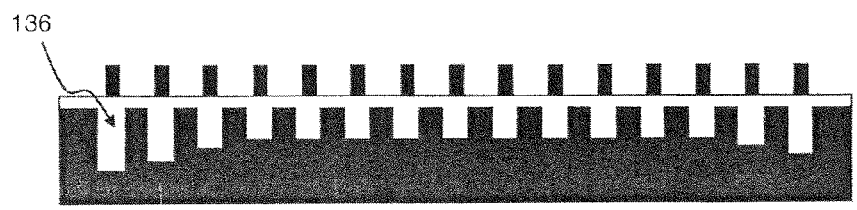
Figure 13C:
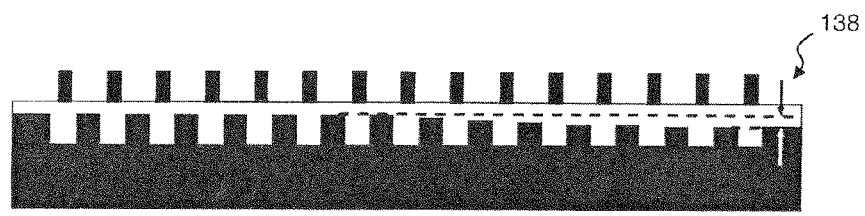
Figure 13D:
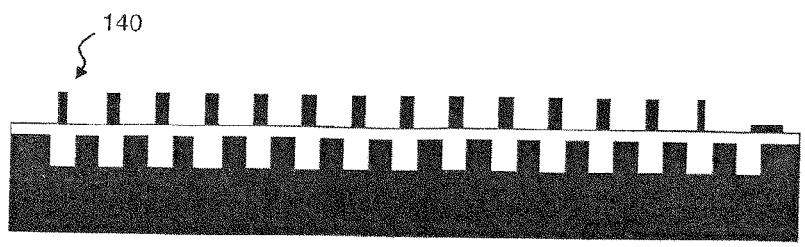

FIG. 12 illustrates horizontal cross sections of the dark-field images along the line AA as shown in FIG. 11, for 10 μm targets with environments that are unpatterned 12a, lines 12b, lines but with an unpatterned rectangle next to the grating (also referred to as "torture") 12c, asymmetric contact holes 12d and contact holes with an unpatterned rectangle next to the grating 12e. In FIG. 12, the horizontal axis is the x-pixel coordinate, X, and the vertical axis is detected intensity, I, in arbitrary units (a.u.). Peaks in the plots correspond to the spot edge diffraction 122 and the lines environment 124.

It can be observed in FIG. 12 that the overlay grating with a lines environment 12b has the best homogeneous diffraction efficiency, with a plateau in the range of X from 425 to 447, corresponding to homogeneous properties of the grating. Environments that are unpatterned 12a, are contact holes 12d and that have unpatterned rectangles 12c, 12e (tortured) have an effect of micro-loading on the overlay grating. They show enhanced diffraction efficiency towards the edges 126, or in the case of tortured lines 12c, just at the side 128 of the unpatterned rectangle.

FIG. 13 illustrates examples that are detectable by an embodiment of the present invention: (a) ideal regular resist grating 132 on an etched lower grating 134, (b) etch loading that results in trench depth variation 136, (c) CMP dishing 138, and (d) litho non-optimal array edge compensation resulting in CD variation towards the target edge 140.

FIG. 14 is a flow chart showing a method of detecting process variation in a structure on a substrate in accordance with an embodiment of the present invention. This may be performed using the apparatus described with reference to FIGS. 5 to 7.

A beam of radiation is directed 142 onto the substrate so as to illuminate the structure and to form an image. All except one order of diffracted radiation are prevented from being detected 144. Thus only part of the spatial frequency spectrum of the diffracted radiation is transmitted to the detector. Only one diffraction order is transmitted. In a preferred embodiment this is the +1st or the −1st diffraction order, however this may, for example, be other single diffraction orders such as $0^{th}$, $2^{nd}$ or $3^{rd}$. An intensity variation across the detected portion is determined 146, corresponding to variation in diffraction efficiency across the structure. The image is thus spatially filtered in a spectrum plane image plane and all except one order of diffracted radiation is prevented by spatial frequency filtering from contributing to the detected image. In other words this is performed in the spectrum of the image (i.e., the Fourier transformed image), and spatial frequency filtering is applied. Process-induced variation in the structure is identified 148 using the determined intensity variation.

Variations in the local diffraction efficiency may be immediately visualized in the images with a resolution of the order of the point-spread-function of the imaging system. The resolution can for example attain λ/NA~1 μm for a wavelength λ=500 nm and a numerical aperture of NA=0.5. The local diffraction efficiency is directly related to the local properties of the grating such as etch-depth of the bottom grating.

The determined intensity variation across the detected portion corresponding to variations in local diffraction efficiency can be processed in different ways:

1. Manual inspection of the images.
2. Automated algorithm, averaging or comparing the intensity profile in 1 or 2 dimensions, e.g., via principal component analysis (PCA)-based methods. Here, higher order terms are an indicator for deviation from an expected constant profile.
3. Statistical analysis for deviation of a flat profile over a set of markers. Indicators are for example variance and standard deviation of the intensities over the markers.
4. Comparison of absolute diffraction intensities of small (grating) structures of micro-meter scale with nearby large diffraction structures with a-priori the same local properties.
5. Definition of a "region of interest" (ROI) to be used for the measurement analysis of the actual target, excluding the regions with too large deviation from the diffraction efficiency of the preferred region (usually the centre) of the metrology target (see FIG. 15 in which the dotted circle illustrates selection of the region of interest (ROI) for metrology purposes). This step is shown in FIG. 14, where a region of interest of the detected portion is selected 150 excluding an unwanted region of the detected portion corresponding to a region of the structure with unwanted process variation and only the selected region of interest is used for a measurement of the structure, while excluding the unwanted region.

The present invention is not limited to specially designed diffraction markers, but can be used on any suitable, locally repetitive structure, including, but not limited to 1D-(lines) or 2D-structures, repetitive product structures and process segmented image based overlay marks.

Additional to $+1^{st}$ or $-1^{st}$ diffraction order transmission and detection, the present invention also includes detection via other diffraction orders, such as $0^{th}$ or $2^{nd}$ or higher orders, of which the most sensitive may be chosen if experimentally accessible. The $0^{th}$ order detection may be attractive for repetitive structures, such as gratings, with small pitch.

Embodiments of the present invention allow micro-loading and process effects inspection in-line with (dark-field) overlay detection, CD-reconstruction, and focus-dose measurements by scatterometry.

Embodiments of the present invention allow micro-loading and process effects inspection faster than additional inspection steps using optical microscopy or top-down SEM.

Embodiments of the present invention provide non-destructive inspection and visualization of micro-loading and process effects at micrometer scale compared to TEM or cross-section SEM.

Embodiments of the present invention enable measurement of large amount of data on a single wafer, which is a statistically relevant population.

Embodiments of the present invention are model-free compared to reconstruction based techniques used to inspect process effects.

Embodiments of the present invention enable more accurate metrology in the dark-field mode, such as an overlay, CD or focus-dose measurement, by defining a ROI that excludes the regions of the metrology targets that suffer from micro-loading and other process-related effects.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of determining a focus of a lithographic apparatus used in a lithographic process on a substrate, the method comprising:
    forming a periodic structure on the substrate, the periodic structure comprising at least one feature having a profile which has an asymmetry, the asymmetry depending on the focus of the lithographic apparatus on the substrate;
    stopping, using a stop arrangement and an illumination arrangement together, zero order diffracted radiation from contributing to a first image and a second image of the periodic structure;
    detecting a first image of the periodic structure while illuminating the periodic structure with a first beam of radiation from the illumination arrangement to generate a first measurement, the first image being formed using a first part of non-zero order diffracted radiation while excluding zero order diffracted radiation;
    detecting a second image of the periodic structure while illuminating the periodic structure with a second beam of radiation from the illumination arrangement to generate a second measurement; the second image being formed using a second part of the non-zero order diffracted radiation which is symmetrically opposite to the first part in a diffraction spectrum;
    determining the asymmetry in the profile of periodic the structure based on the first and second images detected in the first and second measurements; and
    providing an indication of the focus on the substrate based on the determined asymmetry and a relationship between the focus and the determined asymmetry.

2. The method according to claim 1, in which the first and second parts of the non-zero diffraction orders are different ones of at least a portion of each of +1st and −1st orders.

3. The method according to claim 1, wherein an area of the periodic structure is less than at least one of an area of the first beam of radiation and an area of the second beam of radiation on the substrate.

4. The method according to claim 1, wherein the first and second symmetrically opposed parts of the non-zero order diffracted radiation comprise +1 and −1 order diffracted radiation.

5. The method according to claim 1, wherein, in, an optical system used in the first and second measurements, the first, and second beams of radiation have angles of incidence on the periodic structure which are symmetrically off-axis with respect to the optical system, and the first and second images are formed and detected using radiation which is diffracted by the periodic structure into a narrower range of angles centered on an optical axis.

6. The method according to claim 1, further comprising:
    repeating the first and second measurements a plurality of times for structures formed by the lithographic apparatus using different focus values, the structures each comprising at least one feature having a profile which has an asymmetry, the asymmetry depending on the focus of the lithographic apparatus on the substrate; and
    using the images detected in the repeated first and second measurements in determining the relationship between the asymmetry and the focus on the substrate.

7. The method according to claim 1, wherein the determining comprises:
    measuring an intensity of selected portions of the first and second, images.

8. The method according to claim 6, further comprising:
    determining the relationship between the asymmetry and the focus on the substrate using lithographic simulations.

9. The method according to claim 7, further comprising:
    repeating the first and second measurements a plurality of times for structures formed by the lithographic apparatus using different focus values, the structures each comprising at least one feature having a profile which has an asymmetry, the asymmetry depending on the focus of the lithographic apparatus on the substrate; and
    using the images detected in the repeated first and second measurements in determining a relationship between the intensity of the selected portions of the images and the focus on the substrate.

10. The method according to claim 9, further comprising:
    determining the relationship between the intensity of the selected portions and the focus on the substrate using lithographic simulations.

11. An angularly resolved scatterometer configured to determine a focus of a lithographic apparatus used in a lithographic process on a substrate, wherein the lithographic process is used to form a structure on the substrate, the structure comprising at least one feature having a profile which has an asymmetry, the asymmetry depending on the focus of the lithographic apparatus on the substrate, the scatterometer comprising:
    an illumination arrangement configured to deliver first and second beams of radiation to the substrate for use in first and second measurements;
    a detection arrangement operable during the first and second measurements to form and detect respective first and second images of the structure using radiation diffracted from the substrate; and
    a stop arrangement within the detection arrangement, wherein the illumination arrangement and stop arrangement together are effective to stop zero order diffracted radiation contributing to the first and second images, while the first and second images are formed using first and second parts respectively of non-zero order diffracted radiation, the first and second parts being symmetrically opposite one another in a diffraction spectrum of the diffracted radiation; and
    a computational arrangement configured to determine the asymmetry for the feature from the first and second images and/or to use the determined asymmetry and a relationship between the focus and the asymmetry for each feature to provide an indication of the focus on the substrate.

12. The scatterometer according to claim 11, in which, when the structure has a certain periodicity, the detection arrangement is configured to measure +1st and −1st orders as the first and second, parts of the diffracted radiation.

13. The scatterometer according to claim 11, wherein the computational arrangement is configured to compare selected portions of the first and second images, when an area of the structure is less than an area of the substrate represented in the first and second images.

14. The scatterometer according to claim 11, wherein the first and second symmetrically opposed parts of the non-zero order diffracted radiation comprise substantially +1 and −1 order radiation.

15. The scatterometer according to claim 11, wherein, in an optical system used in the measurements, the first and second beams of radiation have angles of incidence on the structure which are symmetrically off-axis with respect to the optical system, and the first and second images are formed and detected using radiation which is diffracted by the structure into a narrower range of angles centered on an optical axis.

16. The scatterometer according to claim 11, wherein the computational arrangement is configured to:
   select and compare respective portions of the first and second images for each of a plurality of structures formed using different focus values, each structure comprising at least one feature having, a profile which has an asymmetry, the asymmetry depending on the focus of the lithographic apparatus; and
   use the selected portions of the images in determining a relationship between the asymmetry and the focus on the substrate.

17. The scatterometer according to claim 11, in which the asymmetry is determined from measuring an intensity of the first and second images of the structure.

18. The scatterometer according to claim 16, wherein lithographic simulations are used in the determination of the relationship between the asymmetry and the focus on the substrate.

19. The scatterometer according to claim 17, wherein the computational arrangement is configured to:
   select and compare respective portions of the first and second images for each of a plurality of structures formed using different focus values, each structure comprising at least one feature having a profile which has an asymmetry, the asymmetry depending on the focus of the lithographic apparatus; and use the selected portions of the images in determining a relationship between the intensity of the selected portions and the focus on the substrate.

20. The scatterometer according to claim 19, wherein lithographic simulations are used in the determination of the relationship between the intensity of the selected portions and the focus on the substrate.

21. A lithographic system comprising:
   a lithographic apparatus comprising:
      an illumination optical system arranged, to illuminate a pattern;
      a projection optical system arranged to project an image of the pattern on to a substrate; and
      an angularly resolved scatterometer configured to determine a focus of the lithographic system used in a lithographic process on the substrate, wherein the lithographic process is used to form a structure on the substrate, the structure comprising at least one feature having a profile which has an asymmetry which depends on the focus of the lithographic system on the substrate, the scatterometer comprising:
         an illumination arrangement configured to deliver first and second beams of radiation to the substrate for use in first and second measurements;
         a detection arrangement operable during the first and second measurements to form and detect respective first and second images of the structure using radiation diffracted from the substrate; and
         a stop arrangement within the detection arrangement, wherein the illumination arrangement and stop arrangement together are configured to stop zero order diffracted radiation contributing to the first and second images, while the first and second images are formed using first and second parts respectively of non-zero order diffracted radiation, the first and second parts being symmetrically opposite one another in a diffraction spectrum of the diffracted radiation; and
         a computational arrangement configured to determine the asymmetry for the feature from the first and second images and/or to use the determined asymmetry and a relationship between the focus and the asymmetry or each feature to provide an indication of the focus on the substrate.

22. A lithographic cell comprising:
   a coater arranged to coat a substrate with a radiation sensitive layer;
   a lithographic apparatus arranged to expose images onto the radiation sensitive layer of the substrate;
   a developer arranged to develop images exposed by the lithographic apparatus; and
   an angularly resolved scatterometer configured to determine a focus of the lithographic apparatus used in a lithographic process on the substrate, wherein the lithographic process is used to form a structure on the substrate, the structure comprising at least one feature having a profile which has an asymmetry, the asymmetry depending on the focus of the lithographic apparatus on the substrate, the scatterometer comprising:
      an illumination arrangement operable to deliver first and second beams of radiation to the substrate for use in first and second measurements;
      a detection arrangement operable during the first and second measurements to form and detect respective first and second images of the structure using radiation diffracted from the substrate; and
      a stop arrangement within the detection arrangement, wherein the illumination arrangement and stop arrangement together are configured to stop zero order diffracted radiation contributing to the first and second images, while the first and second images are formed using first and second parts respectively of non-zero order diffracted radiation, the first and second parts being symmetrically opposite one another in a diffraction spectrum of the diffracted radiation; and
      a computational arrangement configured to determine the asymmetry for the feature from the first and second images and/or to use the determined asymmetry and a relationship between the focus and the asymmetry for each feature to provide an indication of the focus on the substrate.

23. An angularly resolved scatterometer configured to determine a focus of a lithographic apparatus used in a lithographic process on a substrate, wherein the lithographic process is used to form a structure on the substrate, the structure comprising at least one feature having a profile which has an asymmetry, the asymmetry depending on the focus of the lithographic apparatus on the substrate, the scatterometer comprising:
   an illumination device configured to produce a beam of radiation;
   a masking device arranged such that the beam of radiation produced by the illumination device and directed onto the substrate through the masking device will illuminate the structure within a first range of angles;

a detection device configured to detect an image produced by radiation diffracted from the structure;

a stop device between the substrate and the detection device, the masking device and stop device together being effective to stop zero order diffracted radiation and a part of higher order diffracted radiation from being detected, wherein the masking device and the substrate are configured to rotate relative to each other about their respective optical axes such that after the relative rotation the structure is illuminated within a second range of angles, the second range being diametrically opposed to the first range within a cross section of the beam of radiation, and wherein the detection device is configured to measure different portions of the image produced by the diffracted radiation produced by directing the beam of radiation onto the structure through the stop device before and after the rotation of the masking device and the substrate relative to each other about their respective optical axes; and a computational device configured to determine the asymmetry for the feature from the different portions of the image measured before and after the rotation of the device and the substrate relative to each other or to use the determined asymmetry and a relationship between the focus and the asymmetry for each feature to provide an indication of the focus on the substrate.

24. The scatterometer according to claim 23, wherein:

the detection device is configured to measure the different portions of the image for each of a plurality of structures formed by the lithographic apparatus using different focus values, each structure having at least one feature having a profile which has an asymmetry which depends on the focus of the lithographic apparatus; and the computational, device is configured to use the detected portions of the images in determining a relationship between an intensity of the measured portions and the focus on the substrate.

* * * * *

UNITED STATES PATENT AND TRADEMARK OFFICE
CERTIFICATE OF CORRECTION

PATENT NO.         : 9,081,303 B2                                    Page 1 of 1
APPLICATION NO.    : 12/846652
DATED              : July 14, 2015
INVENTOR(S)        : Cramer et al.

It is certified that error appears in the above-identified patent and that said Letters Patent is hereby corrected as shown below:

In The Claims
In column 19, line 34, claim 1, after "measurement", please delete ";" and insert --,--.
In column 19, line 38, claim 1, after "profile of", please insert --the--.
In column 19, line 38, claim 1, after "periodic", please delete "the".
In column 20, line 9, claim 7, after "second", please delete ",".
In column 20, line 62, claim 12, after "second", please delete ",".
In column 21, line 48, claim 21, after "arranged", please delete ",".
In column 22, lines 14-15, claim 21, after "asymmetry", please delete "or" and insert --for--.
In column 24, line 4, claim 23, before "device", please insert --masking--.
In column 24, line 15, claim 24, after "computational", please delete ",".

Signed and Sealed this
First Day of March, 2016

Michelle K. Lee
*Director of the United States Patent and Trademark Office*